(12) United States Patent  (10) Patent No.: US 8,404,102 B2
Guo et al.  (45) Date of Patent: *Mar. 26, 2013

(54) METHOD AND APPARATUS FOR RAPID ELECTROCHEMICAL ANALYSIS

(75) Inventors: Sherry Guo, San Jose, CA (US); Alastair M. Hodges, Blackburn South (AU); Ronald C. Chatelier, Bayswater (AU); Bin Zhang, Fremont, CA (US)

(73) Assignee: Lifescan, Inc., Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/829,599

(22) Filed: Jul. 2, 2010

(65) Prior Publication Data

US 2010/0270178 A1  Oct. 28, 2010

Related U.S. Application Data

(63) Continuation of application No. 11/240,797, filed on Sep. 30, 2005, now Pat. No. 7,749,371.

(51) Int. Cl.
 *G01N 27/327* (2006.01)
 *G01N 27/26* (2006.01)
(52) U.S. Cl. ...... 205/792; 205/775; 205/787; 205/777.5
(58) Field of Classification Search ............... 205/777.5, 205/787, 792
 See application file for complete search history.

(56) References Cited

U.S. PATENT DOCUMENTS

| | | | |
|---|---|---|---|
| 5,395,504 A | 3/1995 | Saurer et al. |
| 5,525,297 A | 6/1996 | Dinger et al. |
| 5,609,823 A | 3/1997 | Harttig et al. |
| 5,679,311 A | 10/1997 | Harttig et al. |
| 5,727,548 A | 3/1998 | Hill et al. |
| 5,797,693 A | 8/1998 | Jaeger et al. |
| 5,904,898 A | 5/1999 | Markart |
| 5,942,102 A | 8/1999 | Hodges et al. |
| 6,027,689 A | 2/2000 | Markart et al. |
| 6,180,063 B1 | 1/2001 | Markart et al. |
| 6,193,873 B1 | 2/2001 | Ohara et al. |
| 6,299,757 B1 | 10/2001 | Feldman et al. |
| 6,325,917 B1 | 12/2001 | Maxwell et al. |
| 6,475,372 B1 | 11/2002 | Ohara et al. |
| 6,676,995 B2 | 1/2004 | Dick et al. |
| 6,689,411 B2 | 2/2004 | Dick et al. |
| 6,716,577 B1 | 4/2004 | Yu et al. |
| 6,749,887 B1 | 6/2004 | Dick et al. |
| 6,780,645 B2 | 8/2004 | Hayter et al. |
| 6,830,934 B1 | 12/2004 | Harding et al. |
| 2002/0053523 A1 | 5/2002 | Liamos et al. |
| 2002/0150501 A1 | 10/2002 | Robertson et al. |

(Continued)

FOREIGN PATENT DOCUMENTS

AU  54873/94  8/1994
DE  3708031 B1  11/1987

(Continued)

OTHER PUBLICATIONS

Japanese Office Action, Mailed Jun. 14, 2011.

(Continued)

*Primary Examiner* — J. Christopher Ball
*Assistant Examiner* — Jennifer Dieterle
(74) *Attorney, Agent, or Firm* — Hiscock & Barclay, LLP

(57) ABSTRACT

Methods and apparatus for electrochemically determining an analyte concentration value in a physiological sample are disclosed. The methods include using a test strip in which two time-current transients are measured by a meter electrically connected to an electrochemical test strip. Integrative current values are derived from the time-current transients and used in the calculation of analyte concentration.

32 Claims, 4 Drawing Sheets

U.S. PATENT DOCUMENTS

| | | |
|---|---|---|
| 2003/0109798 A1 | 6/2003 | Kermani |
| 2004/0038411 A1 | 2/2004 | Hayter et al. |
| 2004/0050717 A1 | 3/2004 | Teodorczyk et al. |
| 2004/0259264 A1 | 12/2004 | Morita et al. |
| 2005/0164329 A1 | 7/2005 | Wallace-Davis et al. |
| 2005/0176153 A1 | 8/2005 | O'Hara |

FOREIGN PATENT DOCUMENTS

| | | |
|---|---|---|
| EP | 0735363 A1 | 2/1996 |
| EP | 0609760 B1 | 7/1998 |
| EP | 0928967 B1 | 7/1999 |
| EP | 1081490 B1 | 3/2001 |
| EP | 1236995 | 9/2002 |
| JP | 3167464 A | 7/1991 |
| JP | 6222874 | 8/1994 |
| JP | 2001066274 A | 3/2001 |
| JP | 2001183326 A2 | 7/2001 |
| JP | 2001516025 A | 9/2001 |
| JP | 2003240747 A | 8/2003 |
| JP | 2005526260 A | 9/2005 |
| SU | 1351627 A2 | 11/1987 |
| WO | 94/19684 A1 | 9/1994 |
| WO | 97/18465 A1 | 5/1997 |
| WO | 99/32881 A1 | 7/1999 |
| WO | 99/60391 A1 | 11/1999 |
| WO | 0157510 A2 | 8/2001 |
| WO | 03036285 A | 5/2003 |
| WO | 2004090533 A | 10/2004 |
| WO | 2005054848 A | 6/2005 |
| WO | 2005147990 A | 6/2005 |

OTHER PUBLICATIONS

European Patent Office, Search Report, Mar. 7, 2008, 7 pages.

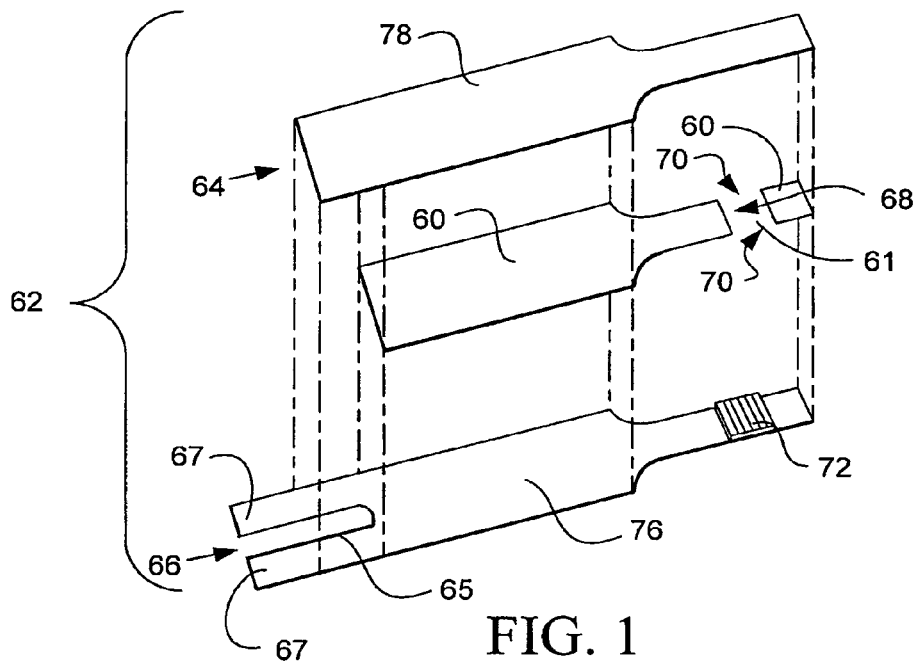
FIG. 1
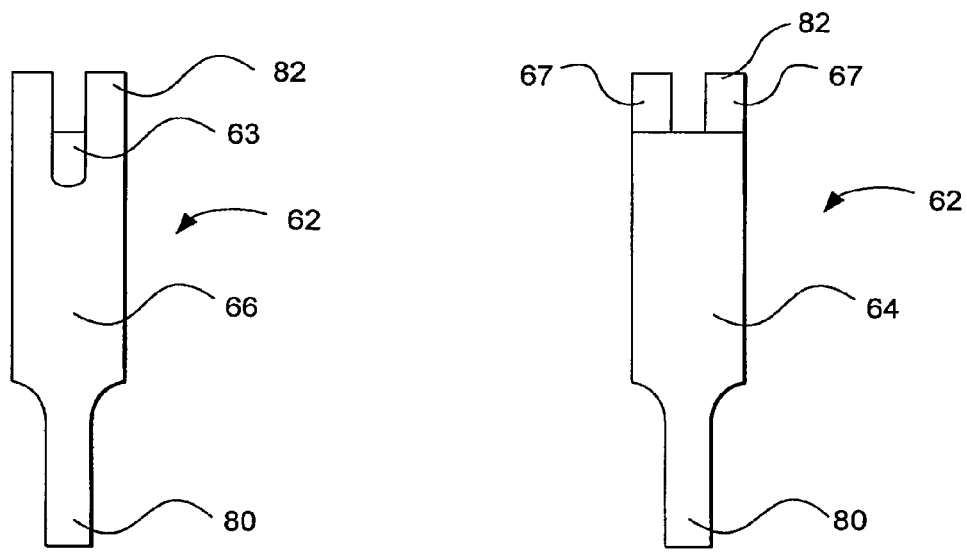
FIG. 2
FIG. 3
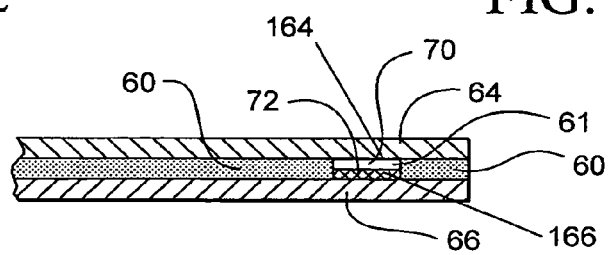
FIG. 4

METHOD AND APPARATUS FOR RAPID ELECTROCHEMICAL ANALYSIS

RELATED APPLICATION

This application claims priority to U.S. patent application Ser. No. 11/240,797, entitled "Method and Apparatus for Rapid Electrochemical Analysis" filed on Sep. 30, 2005, which is hereby incorporated by reference in its entirety.

BACKGROUND OF THE INVENTION

Analyte detection in physiological fluids, e.g. blood or blood-derived products, is of ever increasing importance to today's society. Analyte detection assays find use in a variety of applications, including clinical laboratory testing, home testing, etc., where the results of such testing play a prominent role in diagnosis and management in a variety of disease conditions. Analytes of interest include glucose for diabetes management, ketones, cholesterol (including HDL, LDL, and/or triglycerides), hemoglobin A1C, and the like. In response to this growing importance of analyte detection, a variety of analyte detection protocols and devices for both clinical and home use have been developed.

One type of method that is employed for analyte detection is an electrochemical method. In such methods, an aqueous liquid sample is placed into a sample reaction chamber in a test strip, in this case an electrochemical cell, including two electrodes, i.e. a first and second electrode, where the electrodes have an impedance, which renders them suitable for amperometric measurement. The component to be analyzed is allowed to react directly with an electrode, or directly or indirectly with a mediator to form an oxidizable (or reducible) substance in an amount corresponding to the concentration of the component to be analyzed, i.e. analyte. The quantity of the oxidizable (or reducible) substance present is then estimated electrochemically and related to the amount of analyte present in the initial sample.

One strategy which may be used to quantify the analyte is to allow the analyte to become substantially depleted within the electrochemical cell before electrochemically measuring an oxidizable (or reducible) substance. However, under certain conditions this process may require an extended time period to reach depletion. Other strategies for quantifying the analyte rely on a shorter waiting period. For example, an oxidation current (or reduction current) can be measured over a time period less than that required for complete depletion and the concentration is calculated by extrapolating the collected data. While shorter calculation procedures meet the desire for expedient analysis (especially in the case of glucose monitoring) such methods may lack the desired accuracy. Therefore, it would be desirable to develop a method for quickly and accurately measuring the concentration of an analyte in an electrochemical cell.

SUMMARY OF THE INVENTION

The present invention generally provides methods and apparatus for electrochemically determining an analyte concentration in a physiological sample. In one aspect, described herein, are methods of using a test strip in which two time-current transients (e.g., current as a function of time) are measured by a meter electrically connected to an electrochemical test strip.

The test strip, in one embodiment, includes an electrochemical cell comprising spaced apart working and counter/reference electrodes and a redox reagent. In use, a physiological sample is introduced into the reaction cell where the sample begins to react with the redox reagent. A first electric potential, having a first polarity, is applied to the reaction cell between the working and the counter/reference electrode and cell current as a function of time is measured to obtain a first time-current transient. A second time-current transient is then measured based upon a second electric potential applied to the cell, having a second polarity.

In a first embodiment, a preliminary analyte concentration is derived from the first and/or second time current transients with a curve fitting process and corrected with a correction factor derived from a steady state current value and a pre-pulse current value ($i_{ss}$ and $i_{pp}$, respectively). The ratio of these values is used in an empirically derived equation to calculate the correction factor.

In another embodiment, an integral or summation, of at least a portion of, the data collected from the first and second time-current transients provides first and second integrative current values. These integrative current values are used to find the correction factor. The integrated current values are more stable and can be found without complex calculations.

In yet another embodiment, integrative current values are used to find the initial analyte concentration and the correction factor. The method includes using an integrative current value as the initial analyte concentration and a ratio of integrative current values for the correction factor. The calculation of initial analyte concentration and the correction factor can thus be rapidly calculated directly from the time-current transient data without the need for time intensive calculations. Moreover, the resulting analyte concentration is highly accurate.

For example, the method can include the steps of introducing a physiological sample into an electrochemical cell comprising first and second electrodes in a spaced apart relationship and a reagent layer comprising an enzyme and a mediator. With the sample in position, a first electric potential having a first polarity is applied to the reaction cell. Cell current as a function of time is measured to obtain a first time-current transient. A second electric potential having a second polarity is then applied to the cell, wherein cell current as a function of time is measured to obtain a second time-current transient. A first integrative current value is calculated from the second time-current transient, the first integrative current value being proportional to the analyte concentration (This first integrative current value provides the initial analyte concentration). A second integrative current value is derived from the second time-current transient and a third integrative current value is derived from the first time-current transient. These integrative current values are used to calculate a correction factor. Analyte concentration is then derived by multiplying the first integrative current value by the correction factor.

In one aspect, the integrative current values comprise an integral of cell current as a function of time. Alternatively, the integrative current values comprise a summation of cell current as a function of time. In yet another aspect, the integrative current values are a product of an average or single current value of a time-current transient multiplied by a time interval of the time-current transient. The first, second, and third integrative current values can be calculated during any portion of their respective time-current transients. Alternatively, the integrative current value can be found from measuring cell charge over time. For example, integrative columbic values can be determined and used in the same manner as the integrative current values.

In a further embodiment, analyte concentration is calculated based upon the equation $[C]=(I_2/I_3)^P*(a*I_1-Z)$, where

[C] is analyte concentration, $I_1$ is the first integrative current value, $I_2$ is the second integrative current value, and $I_3$ is the third integrative current value. Z is a background value that can remove the effect of background currents. To account for variations in the electrochemical cell in which the method is performed, the above equation includes empirical parameters. For example, the ratio $(I_2/I_3)$ is to the power p and $I_1$ is multiplied by a constant a. The value of these parameters can be determined for each electrochemical cell or for a set of electrochemical cells.

In one embodiment, the first electric potential has a first polarity opposite the second electric potential. For example, the first polarity can be negative and the second polarity positive. The first electric potential can be in the range of about 0.0 to −0.6 V and the second electric potential can be in the range of about 0.0 to 0.6 V. In one aspect, the first and second electric potentials are each applied for a duration of time in the range of about 1 second to 5 seconds.

The analyte measured with the method disclosed herein, is in one embodiment, glucose. For example, the concentration of glucose in a physiological sample of whole blood, plasma, serum, interstitial fluid, or urine can be measured. The mediator used in the analysis of glucose can, for example, be ferricyanide, ferrocene, ferrocene derivatives, osmium bipyridyl complexes, and/or quinone derivatives.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 shows an exploded perspective view of a test strip suitable for use in the present invention;

FIG. 2 is a bottom plan view of the test strip;

FIG. 3 is a top plan view of the test strip;

FIG. 4 is a partial cross-sectional side view of a distal portion of the test strip;

DETAILED DESCRIPTION OF ILLUSTRATIVE EMBODIMENTS OF THE INVENTION

Figure 5:
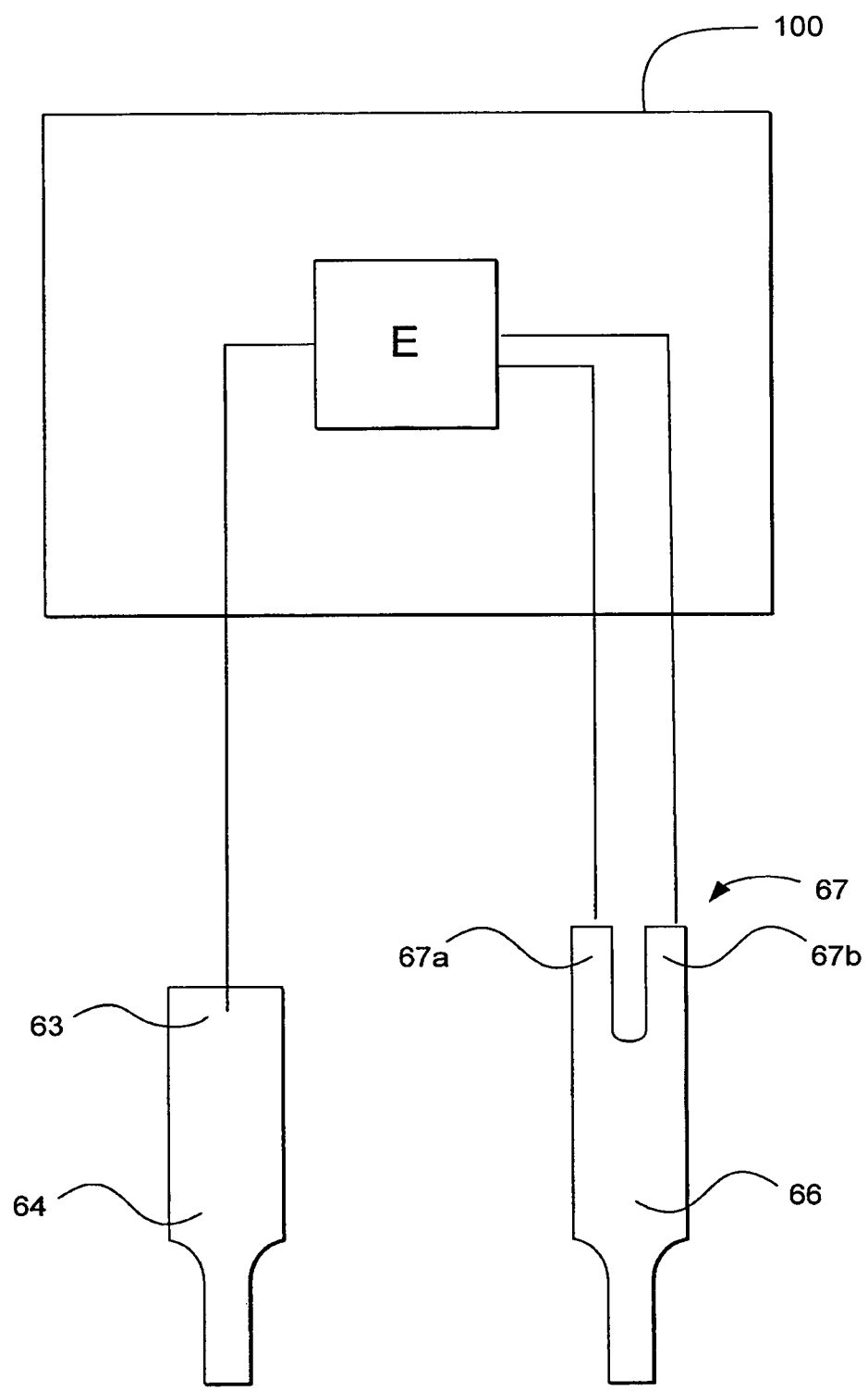
FIG. 5 is a simplified schematic showing a meter electrically interfacing with the test strip.

The subject methods and devices are suited for use in the determination of a wide variety of analytes in a wide variety of samples, and are particularly suited for use in the determination of analytes in whole blood or derivatives thereof, where an analyte of particular interest is glucose. The subject invention provides methods for determining an analyte concentration value in a physiological sample in a rapid manner and with accurate results. Described herein are structures of an exemplary test strip embodiment which can be used in measuring an analyte concentration value. Further, described herein are methods of using the test strip in which a time-current transient is measured and collected by a meter electrically connected to the test strip. Yet further described herein are algorithms which are used to process the time-current transient in a rapid manner and which output accurate analyte concentration values.

The subject methods may be used, in principle, with any type of electrochemical cell having spaced apart first and second electrodes and a reagent layer, such as for example, an electrochemical test strip. In one aspect, an electrochemical test strip includes two opposing electrodes separated by a thin spacer layer, where these components define a sample reaction chamber or zone in which is located a reagent layer.

FIGS. 1 to 4 show an exploded perspective view, a bottom view, a top view, and a cross-sectional side view, respectively, of an exemplary test strip 62 suitable for use with the method described herein. Test strip 62 includes a first electrode layer 66, a spacer 60, a second electrode layer 64, a distal portion 80, and a proximal portion 82. When fully assembled, test strip 62 has a sample reaction chamber 61 for receiving a sample. In one aspect, sample reaction chamber 61 is formed by cutout area 68 in spacer 60, second electrode layer 64, and first electrode layer 66. Physiological fluid can be delivered through a port 70, and in one embodiment, there are two ports 70. In one aspect, one of the ports 70 can provide a sample inlet and the other can act as a vent.

In the illustrated embodiment, first electrode layer 66 and second electrode layer 64 are spaced apart in a facing or opposing faced arrangement. However, one skilled in the art will appreciate that the electrodes can be positioned in a variety of ways including in coplanar and non-coplanar configurations.

A portion of first electrode layer 66 and second electrode layer 64 can provide electrodes 166, 164, respectively. For example, the portion of first electrode layer 66 and second electrode layer 64 exposed within reaction chamber 61 can define first electrode 166 and second electrode 164. In addition, first electrode layer 66 can include a first electrical contact 67 and a U-shaped notch 65 as illustrated in FIG. 1. First electrical contact 67, which is electrically connected to first electrode 166 via a first connection track 76, is used to establish an electrical connection to a meter. Second electrode layer 64 may include a second electrical contact 63 which is electrically interconnected with second electrode 164 via a second connection track 78 as illustrated in FIGS. 1 through 3. Second electrical contact may be accessed by a meter through U-shaped notch 65 as illustrated in FIG. 1. One skilled in the art will appreciate that test strip 62 can include a variety of alternative electrical contact configurations for electrically connecting to a meter. For example, U.S. Patent No. 6,379,513 discloses electrochemical cell connection means, and is hereby incorporated by reference in its entirety.

In one embodiment, the first and/or second electrode layers may be a conductive material formed from materials such as gold, palladium, carbon, silver, platinum, tin oxide, iridium, indium, and combinations thereof (e.g., indium doped tin oxide). In addition, the electrodes can be formed by disposing a conductive material onto an insulating sheet (not shown) by a sputtering, electroless plating, or a screen printing process. In one exemplary embodiment, second electrode 64 layer may be a sputtered gold electrode and first electrode layer 66 may be a sputtered palladium electrode. Suitable materials that may be employed as the insulating sheet include, for example, plastics (e.g. PET, PETG, polyimide, polycarbonate, polystyrene), silicon, ceramic, glass, and combinations thereof.

A reagent layer 72 can be disposed within reaction chamber 61 using a process such as slot coating, coating by dispensing liquid from the end of a tube, ink jetting, and screen printing. Such processes are described, for example, in the following U.S. Pat. Nos. 6,749,887; 6,689,411; 6,676,995; and 6,830,934, which are hereby incorporated by reference in their entirety. In one embodiment, reagent layer 72 is deposited onto first electrode 166 and includes at least a mediator and an enzyme. A mediator can be in either of two redox states which may be referred to as an oxidizable substance or a reducible substance. Examples of suitable mediators include ferricyanide, ferrocene, ferrocene derivatives, osmium bipyridyl complexes, and quinone derivatives. Examples of suitable enzymes include glucose oxidase, glucose dehydrogenase (GDH) based on a pyrroloquinoline quinone co-factor, and GDH based on a nicotinamide adenine dinucleotide co-factor. One exemplary reagent formulation, which would be suitable for making reagent layer 72, is described in pending U.S. application Ser. No. 10/242,951, entitled, Method for Manufacturing a Sterilized and Calibrated Biosensor-Based Medical Device, published as U.S. Published Patent Application No. 2004/0120848, which is hereby incorporated by reference in its entirety.

In one embodiment, sample reaction chamber 61 is defined by first electrode 166, second electrode 164, and spacer 60 as shown in FIGS. 1 to 4. Specifically, first electrode 166 and second electrode 164 define the top and bottom of sample reaction chamber 61, while the spacer layer defines the side walls of sample reaction chamber 61. For example, spacer 60 may include a cutout area 68 that defines a sample reaction chamber 61 for test strip 62.

The height of spacer 60 can define the distance between first electrode 166 and second electrode 164. In one aspect, the height of spacer 60 is in the range of about 1 micron to 500 microns, preferably between about 10 and 400 microns, and more preferably between about 40 microns and 200 microns.

In one embodiment, test strip 62 includes first electrode 166 and second electrode 164 positioned such that they are separated by only a short distance. In such a scenario, redox cycling can occur in which the oxidized mediator generated at first electrode 166 can diffuse to second electrode 164 to become reduced and subsequently diffuse back to first electrode 166 to become oxidized again.

Either first electrode 166 or second electrode 164 may perform the function of a working electrode which oxidizes or reduces a limiting amount of mediator depending on the applied polarity of the meter. For example, if the current limiting species is a reduced mediator, then it can be oxidized at first electrode 166 as long as a sufficiently positive potential is applied with respect to second electrode 164. In such a situation, first electrode 166 performs the function of the working electrode and second electrode 164 performs the function of a counter/reference electrode.

Similarly, if a sufficiently negative potential is applied with respect to second electrode 164, then the reduced mediator can be oxidized at second electrode 164. In such a situation, second electrode 164 performs the function of the working electrode and first electrode 166 performs the function of the counter/reference electrode.

A first step in the subject methods can include introducing a quantity of the physiological sample of interest into an electrochemical cell that includes spaced apart first and second electrodes and a reagent layer. The physiological sample may vary, but in many embodiments is generally whole blood or a derivative or fraction thereof, where whole blood is of particular interest. The physiological sample, e.g. blood, is dosed into sample reaction chamber 61 via port 70. In one aspect, port 70 and/or reaction chamber 61 are sized such that capillary action causes the physiological sample to fill sample reaction chamber.

FIG. 5 provides a simplified schematic showing a meter 100 interfacing with first electrical contact 67 and second electrical contact 63, which are in electrical communication with first and second electrode 166, 164, respectively, of test strip 62. Meter 100 is adapted to electrically connect to first electrode 164 and second electrode 166, via electrical contact 63 and second electrical contact 67 (as shown in FIGS. 2 and 5). In one aspect, meter 100 makes contact to electrical contact 63 through U-shaped notch 65.

As illustrated in FIG. 5, electrical contact 67 can comprise two prongs, 67a, 67b. In one exemplary embodiment, meter 100 separately connects to prongs 67a, 67b, such that when meter 100 interfaces with test strip 62 a circuit is completed. Meter 100 can use the closed circuit across electrode layer 66 as a signal that the test strip is in place. One skilled in the art will appreciate that meter 100 can use a variety of sensors and circuits to determine when test strip 62 is properly positioned with respect to the meter.

In one embodiment, first electrical contact 67 and second electrical contact 63 connect to a voltage source E. When performing a test, voltage source E applies a first electric potential between first electrode 166 and second electrode 164 for a first time interval. The first electric potential can be applied immediately after physiological sample is detected as being present in the sample reaction chamber. In one aspect, the physiological sample may be detected by an automatic technique in which the meter monitors a change in voltage (e.g., as described in U.S. Pat. No. 6,193,873), current, or capacitance, a change in which indicates that sample has been dosed into the sample reaction chamber. Alternatively, the physiological sample may be detected by a manual technique in which the user visually observes the filling of the sample reaction chamber and initiates the test by pressing a button.

After the sample has entered the cell, a first electric potential, having a first polarity, can be applied to sample reaction chamber 61 and a resulting current measured as a function of time. At least a portion of the data (current as a function of time) provides a first time-current transient. The first electrical potential can be sufficiently negative with respect to second electrode 164 such that second electrode 164 functions as the working electrode in which a limiting oxidation current is measured. After the first time interval has elapsed, voltage source E applies a second electric potential between first electrode 166 and second electrode 164 for a second time interval. The second electrical potential causes a current that is measured as a function of time to produce a second time-current transient. In one embodiment, the second potential has a second polarity, which is opposite to the first polarity. For example, the second potential can be sufficiently positive with respect to second electrode 164 such that first electrode 166 functions as the working electrode in which a limiting oxidation current is measured. In one aspect, the first electric potential and second electrical potential may range from about −0.6 V to about +0.6 V. The time interval of the time-current transients can, in one embodiment, be in the range of about 0.5 second to 10 seconds, and preferably in the range of about 1 to 5 seconds. In another embodiment, a sum of the first time interval and the second time interval is less than about 5 seconds. It should also be noted that the first time interval does not have to be the same as the second time interval.

In one embodiment, the second electric potential is applied immediately following the application of the first electric potential. In an alternative embodiment, a delay or open circuit potential is introduced in between the first electric potential and the second electric potential. In another alternative embodiment, a delay is introduced after physiological sample is detected in the sample reaction chamber, but before the application of the first electric potential. The delay can be in the range of about 0.01 and 3 seconds, preferably between 0.05 and 1 second and most preferably between 0.1 and 0.5 seconds.

Figure 6:
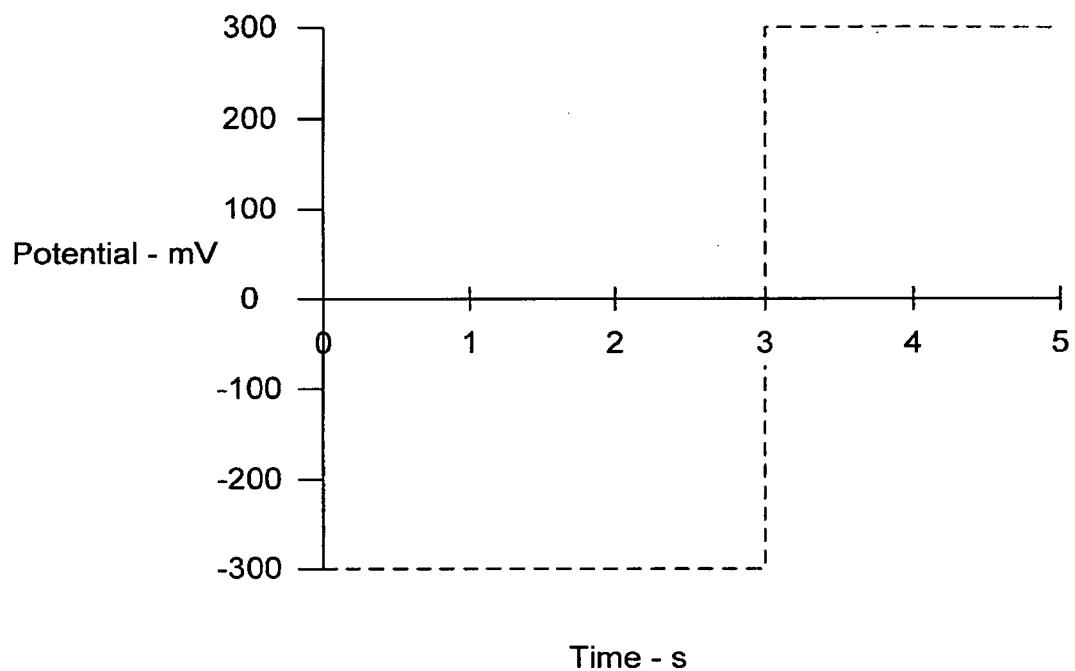
FIG. 6 shows an example of a time-potential waveform having a first electric potential immediately followed by a second electric potential.
Figure 7:
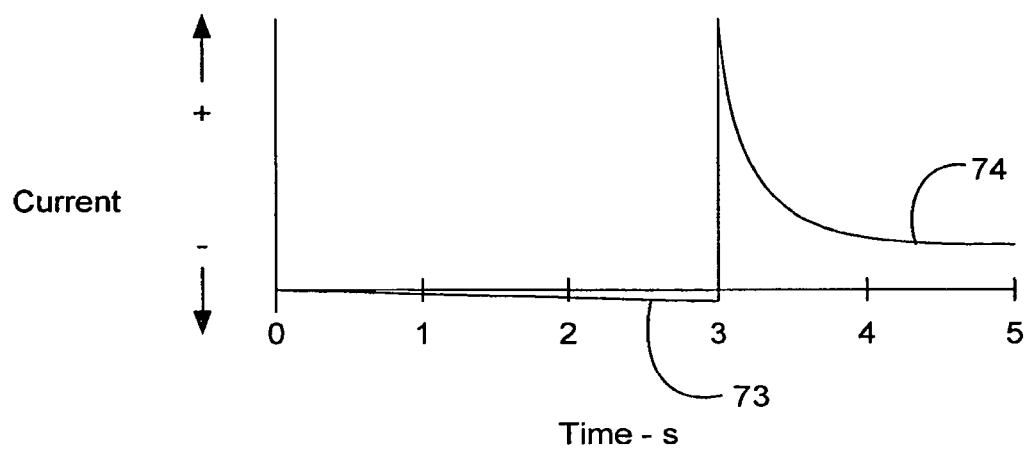
FIG. 7 is a time-current transient generated by a meter that is testing a test strip dosed with a physiological sample.

FIG. 6 shows an example of a time-potential waveform having a first electric potential of −0.3 V for 3 seconds immediately followed by a second electric potential of +0.3 V for 2 seconds. FIG. 7 shows the resulting measured current as a first time-current transient 73 immediately followed by a second time-current transient 74.

In a first embodiment, analyte concentration is determined from measured time current transient data (FIG. 7). The method includes using the first and second time-current transients, obtained as described above, to determine: (a) a variable y; and (b) a preliminary analyte concentration $C_o$ for the analyte of interest in the sample. It should be noted that y is defined as $$\frac{i_{ss}}{i_{pp}}.$$

The term $i_{pp}$ is the average current over a short period of time near the end of first time-current transient. For example, where the first time interval is 3 seconds long, the average current may be the average current from 1.9 to 2.9 seconds of the 3 second long period.

The term $i_{ss}$ is the steady-state current value for the second time-current transient. Because the height of spacer 60 is about less than or equal to the diffusion layer height, the current tends toward a steady-state value. The term $i_{ss}$ may be estimated using Equation 2, for currents at times greater than a minimum time, where a suitable minimum time can be estimated from Equation 1.

$$t_{min} = \frac{-L^2 \ln 0.01}{12\pi^2 D} \quad \text{Eq. 1}$$

$$i(t) = i_{ss}\left\{1 + 4\exp\left(\frac{-4\pi^2 Dt}{L^2}\right)\right\} \quad \text{Eq. 2}$$

in which, $i_{ss}$ the steady-state current following application of the second electric potential; i is the measured current which is a function of time; D is the diffusion coefficient of the redox-active molecule, where this coefficient may be determined from Fick's first law, i.e. J(x,t)=−D dC(x,t)/dx; L is the spacer thickness; and t is the time for the application of the second electric potential where t=0 for the beginning of the pulse.

The preliminary analyte concentration $C_o$ for the analyte of interest in the sample is calculated using the following Equation 3, $$i_{ss} = \frac{2FADC_o}{L} \quad \text{Eq. 3}$$

in which, F is Faraday's constant, i.e. 9.6485×10$^4$C/mol, and A is the area of the first electrode.

Eq. 4 shows the equation used to convert the measured current into an analyte concentration [C] in which CF is the correction factor and Z is a constant which accounts for background currents.

$$[C] = CF \times [C_o - Z] \quad \text{Eq. 4}$$

The term CF can be an empirical equation, based on y and $C_o$, which causes the analyte concentration [C] to be more accurate. An example of a mathematical expression for CF is shown in Eq. 5 in which b, c, and d are constants.

$$CF = \frac{1}{b + \left[\frac{c \times \ln(C_o)}{C_o}\right] + [d \times \ln(y)]} \quad \text{Eq. 5}$$

Therefore, Equations 1 to 5 may be used to calculate an analyte concentration. However, the calculation of $C_o$ and $i_{ss}$ are mathematically intensive and require a relatively fast microprocessor.

A second embodiment provides an algorithm for measuring an analyte concentration that is mathematically simpler and able to provide an accurate analyte concentration.

In one aspect, integrative current values are used in the determination of the correction factor. These integrative current values allow analyte concentration to be more rapidly and accurately determined. Moreover, the integrated current values are generally more robust that current values taken at one point in time.

In one exemplary embodiment, a method of using integrative current values includes applying a first electric potential having a first polarity and measuring cell current as a function of time to obtain a first time-current transient and applying a second electric potential having a second polarity and measuring cell current as a function of time to obtain a second time-current transient. In one aspect, the second polarity is opposite said first polarity. Based on the first time current transient, a first integrative current value is calculated, and based on the second time-current transient, a second integrative current value is calculated. Dividing the second current value by the first current value provides a ratio that can be used in calculating a correction factor. The correction factor and an initial analyte concentration value provide the information necessary for calculating the analyte concentration.

In another embodiment, the calculation of both CF and $C_o$ are avoided. Applicant has found that the initial analyte concentration can be calculated by integration of second pulse measurements within a small time interval. Instead of calculating $C_o$, an integrative current value can be substituted.

For example, to calculate CF and $C_o$, a first integrative current value $I_1$ and a second integrative current value $I_2$ are calculated from the second time-current transient and a third integrative current value $I_3$ is calculated from the first time-current transient. A ratio is then calculated which includes second integrative current value $I_2$ divided by the third integrative current value $I_3$. This ratio provides the correction factor while the first integrative value $I_1$ provides a value that can be substituted from the initial concentration. One skilled in the art will appreciate that names "first," "second," and "third" are chosen for convenience and do not necessarily reflect the order in which the integrative current values are calculated.

To improve the accuracy of the results and reduce the influence of test strip variation a number of empirical parameters can be used. In one aspect, $I_1$ can be multiplied by a constant a and the variable Z can be subtracted from the multiplication product of a and $I_1$, to account for background currents. In another aspect, the ratio $I_2/I_3$ can be set to the power p.

Eq. 6 illustrates the calculation steps.

$$[C] = \left(\frac{I_2}{I_3}\right)^p \times (a \times I_1 - Z) \quad \text{Eq. 6}$$

The substitution of the first, second, and third current values into Eq. 6 allows for accurate analyte concentrations to be determined in a relative short time frame. The time consuming and computer intensive calculation of steady state current and initial analyte concentration are avoided, resulting in simpler analysis and reduced assay test time. In particular, since $I_1$ can be determined based on summation or integration of current values, it requires significantly less computational power compared to a calculation of $C_o$, which requires an iterative algorithm.

In one embodiment, the use of integrated current values can provide for rapid calculation of analyte concentration. For example, the method of applying a first and second electric potential and calculating analyte concentration can be performed in less than about 10 seconds In another embodiment, the analyte concentration can be calculated in less than about 6 seconds, and in yet another embodiment the analyte concentration can be calculated in less than about 5 seconds.

First integrative current value $I_1$ and second integrative current value $I_2$ are, in one aspect, an integral of current values over a time interval of the second time-current transient, a summation of current values over a time interval of the second time-current transient, or an average or single current value of the second time-current transient multiplied by a time interval of the second time-current transient. Similarly, third current value $I_3$ may be an integral of current values over a time interval of the first time-current transient, a summation of current values over a time interval of the first time-current transient, or an average or single current value of the first time-current transient multiplied by a time interval of the first time-current transient. For the summation of current values, a range of consecutive current measurements can be summed together ranging from only two current values to all of the current values.

In another embodiment, first current value, second current value, and third current value can be replaced with a coulombic value. Instead of measuring a current, the passed charge can be measured. The total charge passed provides the same information as integrating time-current data. For example, the charge passed can be measured over a pre-determined time interval and used for the first, second, and/or third current value.

In one aspect, reagent layer 72 is disposed on first electrode 166 and thus generally remains proximate to first electrode 166 after its dissolution with physiological sample. This results, at least initially, in a major proportion of oxidizable substance to be proximate to first electrode 166. After a certain period of time has past, reduced mediator, generated in reagent layer 72 by the reaction of glucose, will passively diffuse away from first electrode 166 to second electrode 164. During the application of the first electrical potential, second electrode 164 oxidizes reduced mediator as it diffuses away from first electrode 166. During this process, the magnitude of the mediator concentration between first electrode 166 and second electrode 164 forms a gradient in which the reduced mediator concentration is higher at the first electrode 166 and lower at second working electrode 164. A large concentration of reduced mediator at first electrode 166 will cause the magnitude of the gradient to become steeper. The magnitude of this oxidation current is proportional to the magnitude of this gradient. Therefore, the amount of reduced mediator generated by reagent layer 72 drives the diffusion of reduced mediator to second electrode 164. The rate of change of the current measured at the electrodes is thus indicative of the rate of change of the reduced mediator concentration at reagent layer 72 and also of the glucose reaction kinetics (i.e. the reaction rate of glucose which generates reduced mediator).

The glucose reaction kinetics depends on several factors that include the height of spacer 60 (as it relates to the maximum distance the glucose has to diffuse to get to the reagent layer 72), viscosity of the physiological sample, hematocrit concentration, and the temperature.

A viscosity increase in the physiological sample can occur with increases in hematocrit, protein, lipid content, or combination thereof. Hematocrit refers to the proportion of red cells in a blood sample. Typically, a higher proportion of red cells causes blood to be more viscous and results in a larger proportion of the total glucose to be inside the red cells. In order for glucose inside the red cells to react with reagent layer 72, the glucose must transport across the red cell membrane. Under certain conditions, this transport may be relatively slow so as to limit the glucose reaction kinetics. Therefore, higher hematocrit slows the glucose reaction kinetics. Viscosity generally slows down the general diffusion process within sample reaction chamber 61. A higher temperature generally increases the reaction rate of glucose with reagent layer 72 within sample reaction chamber 61 as it speeds up the transport processes involved.

In the method disclosed herein, glucose reaction kinetics is accounted for by using time-current transients. The result is less dependence on hematocrit concentration and temperature, and improved accuracy and precision in the determination of glucose concentration.

The magnitude of the second time-current transient will generally be larger than the absolute magnitude of the first time-current transient. Thus, the ratio $I_2/I_3$ will generally be greater than unity, while the glucose reaction is underway within sample reaction chamber 61 and would become unity when the glucose reaction is complete. The departure of the ratio $I_2/I_3$ from unity will therefore be a factor indicating the degree of reaction completion. Relatively large values of $I_2/I_3$ will indicate that the glucose reaction is far from completion whereas $I_2/I_3$ values close to unity will indicate that the glucose reaction is nearly complete. Therefore, the ratio $I_2/I_3$ generally provides information on the progress of the glucose reaction and can be used to eliminate the effect of hematocrit, viscosity, and temperature on the measurement of glucose concentration.

To further refine the calculations, one or more calibration factors can be used. For example, as shown in Eq. 6, the ratio $I_2/I_3$ is set to the exponential p in which p is a calibration factor that can be used for a particular lot of test strips. The use of exponent p was found through empirical means to improve the accuracy and enable rapid test times. In one embodiment of the invention, p may range from about 0.2 to about 4 and preferably between about 0.4 to about 1.

As shown in Eq. 6, a calibration factor a can be used to account for possible variations in cutout area 68 and height of spacer 60. Variations in cutout area 68 can cause a systematic shift in the magnitude of the measured current. Under certain circumstances, manufacturing processes can cause the electrode area to vary from one lot of test strips to another lot of test strips. Similarly, the height of spacer 60 also can vary between lots. Variations in the height of spacer 60 have a proportional impact on the measured current. Calculating a calibration factor a for each lot of test strip helps to compensate for variations in electrode area and the height of spacer 60. The term a can be calculated during the calibration process of a test strip lot.

In one embodiment, as shown in Eq. 6, a calibration factor Z is used to account for variations in the background. A current that is generated from sources other than glucose can contribute to the background signal. For example, if reagent layer 72 were to contain a small amount of oxidizable substance as an impurity before a physiological sample was added to the test strip, then there would be an increase in the measured current (i.e. background) which could not be ascribed to the glucose concentration. Because this would cause a constant bias in the overall measured current for a particular lot of test strips, this bias can be corrected for using the calibration factor Z. Similar to the terms p and a, Z can also be calculated during the calibration process.

While the method disclosed herein is described with the use of calibration factors p, a, and Z, one skilled in the art will appreciate that their use is not required. For example, in one embodiment, glucose concentration could be calculated without p, a, and/or Z (p and/or a could be set equal to one and Z could be set equal to zero).

The selection of the time interval in which $I_1$, $I_2$, and $I_3$ are calculated can be determined with a training algorithm for a particular type of test strip. During the training algorithm, several test strips would be tested over a range of conditions that a user may encounter during testing. Such conditions may include a glucose concentration range from 20 mg/dL to 600 mg/dL, a hematocrit range from 0% to 70%, a temperature range from 5° C. to 45° C., humidity range from 5% relative humidity (% RH) to 95% RH, and endogenous and exogenous interferents. Examples of endogenous and exogenous interferents and their physiological concentration range can be found in the publication entitled National Committee for Clinical Laboratory Standards. Interference testing in clinical chemistry; proposed guideline EP7-P. Wayne, Pa.: NCCLS, 1986 which is incorporated by reference herein. Using standard minimization of error techniques, an optimized selection of time intervals for $I_1$, $I_2$, and $I_3$ was defined such that the calculated glucose concentration using Equation 6 was accurate (e.g., within 10% of reference measurement) and precision (e.g., strip-to-strip variation of about 2% at 1 τ). One skill in the art will appreciate, the chosen time interval for the first and second integrative current values can thus be the same or different, and in one embodiment, only two integrative current values are calculated. The first integrative current value is then used for $I_1$ and $I_2$.

After the time intervals for $I_1$, $I_2$, and $I_3$ are chosen, the strip lot can be calibrated. Exemplary methods for calibrating strip lots are described in U.S. Pat. No. 6,780,645 which is hereby incorporated by reference in its entirety. More particularly, the calibration factors a, p, and/or Z can be calculated for a particular lot of test strips. Typically, a range of glucose concentrations in blood from multiple donors are tested using the glucose test strips and also a reference instrument known to be accurate and precise. The error between the results from the test strips of the present invention and the reference method is minimized by finding the optimal combination of a, p, and/or Z. In one embodiment, the calibration information can be transmitted to a glucose meter before using a test strip from the test strip lot.

In another embodiment the factors controlling the values of a, p and Z can be sufficiently tightly controlled during fabrication that they are the same between lots of strips. The criteria for being able to successfully employ this embodiment is that the multiple lots of strips give a response accuracy within specified limits with the same values of a, p and Z employed in the algorithm. This embodiment obviates the need for a system to transmit the calibration information to the meter as the pre-determined values of a, p and Z can be stored in the meter during manufacture. The main parameters that need to be tightly controlled for this embodiment to have utility is the geometry of the sensor cell (the electrode areas and spacing) and that there is a sufficient excess of glucose reaction activity in the reagents such that the rate of glucose reaction is substantially mass transport controlled rather than chemical reaction rate controlled.

The following examples are illustrative of the principles and practice of this invention. Numerous additional embodiments within the scope and spirit of the invention will become apparent to those skilled in the art.

EXAMPLE 1

A buffer was prepared that contained 100 mM citraconate at pH 6.5, 0.1% anti-foam (RNA Equilibrator), and 4 mM $CaCl_2$. Next, GDH which used a PQQ cofactor, was added to the buffer so that it was 46 mg/mL. PQQ was then added to the buffer so that it could activate the GDH. PQQ was added to the buffer such that there were at least 2 moles of PQQ per mole of GDH. After addition of PQQ, the formulation was allowed to incubate about one hour. Next, potassium ferricyanide was added to the mixture such that it was 800 mM. The formulation was striped onto first electrode 166 as shown in FIG. 1 by means of a slot coating process which is described in U.S. Pat. Nos. 6,749,887; 6,689,411; and 6,676,995 which are hereby incorporated by reference herein. Upon coating the formulation and drying it such that it forms reagent layer 72, spacer 60 and second electrode 164 are assembled thereon to form test strip 62.

EXAMPLE 2

Figure 8:
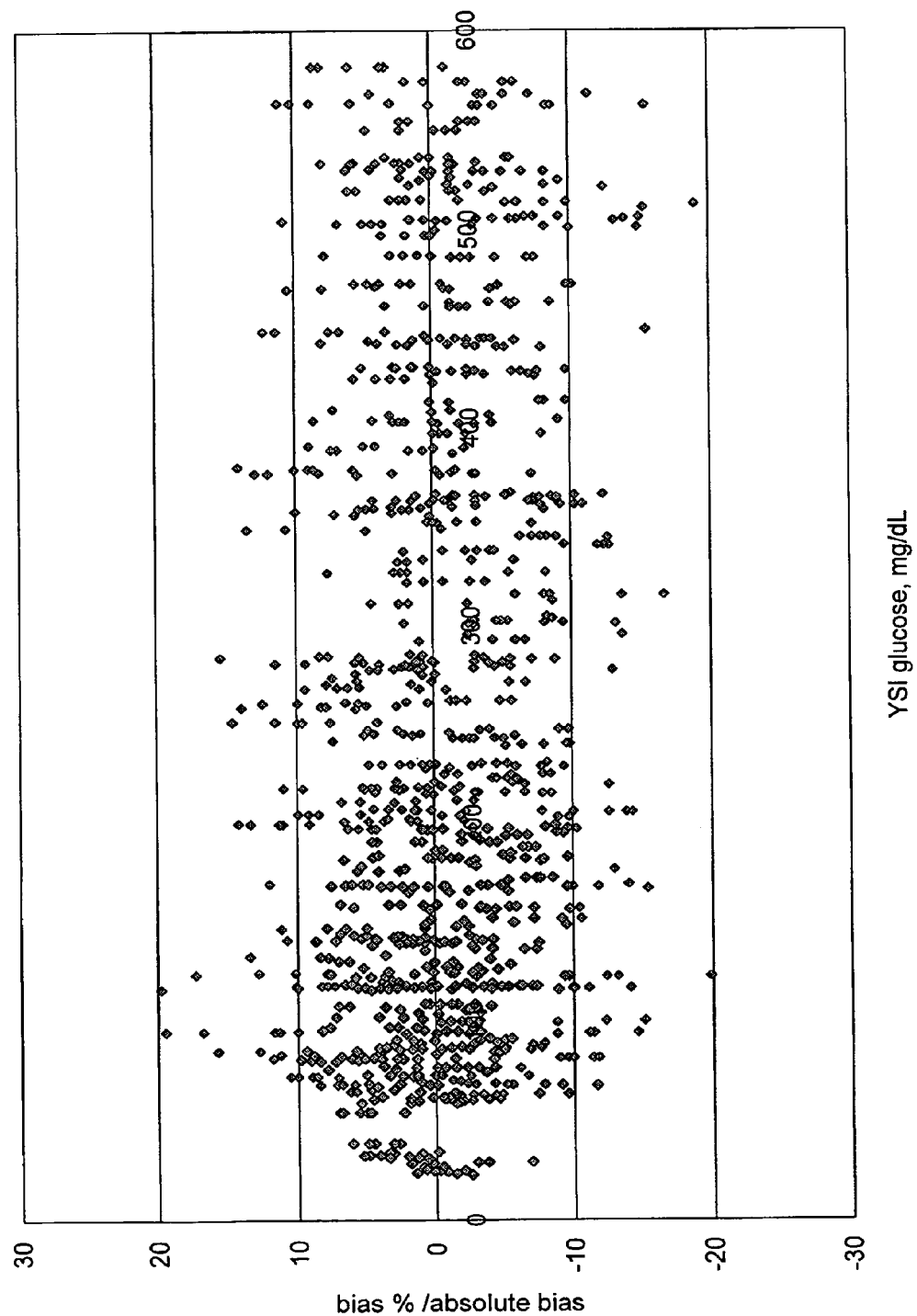
FIG. 8 is a bias graph showing the relationship between glucose concentration and bias to a reference method.

Several test strips 62 were tested with blood for a wide range of glucose concentrations from about 20 mg/dL to about 600 mg/dL in blood. Twenty-three different blood donors were used for this study. Test strips 62 were tested using a five second test time. The measured current was converted to a glucose concentration using Eq. 5. A bias was calculated for each test strip against the reference method. At low glucose concentration (<100 mg/dL), an absolute bias was calculated and at high glucose (≧100 mg/dL), a percent bias was calculated. FIG. 8 shows that 93% of the data points have a bias less than or equal to 10% or 10 mg/dL.

A first potential was applied between the electrodes with the reagent coated electrode being −300 mV with respect to the other electrode for 4.0 seconds, the potential was then reversed such that the reagent coated electrode was at +300 mV with respect to the other electrode for 1 second. The current values at 50 ms intervals were measured and stored. To perform this analysis the first integrative current value $I_1$ was obtained by summing the stored current values between 4.8 and 5.0 seconds after the potential was reversed. $I_2$ was similarly obtained by summing the current values between 4.7 and 5.0 seconds after the potential was reversed and $I_3$ by summing the current values between 1.6 and 4.0 seconds after the original potential was applied. The values of a, p and Z were determined empirically and were 1.29, 0.645 and 3.64 respectively.

As shown in FIG. 8, using first, second, and third integrative current values to calculate analyte concentration provided accurate concentration information in a rapid manner.

It will be recognized that equivalent structures may be substituted for the structures illustrated and described herein and that the described embodiment of the invention is not the only structure which may be employed to implement the claimed invention. One example of an equivalent structure, which may be used to implement the present invention, is described in U.S. Pat. No. 6,413,410, which is hereby incorporated by reference in its entirety. Further example of an equivalent structure, which may be used to implement the present invention, are descried in U.S. Pat. Nos. 6,612,111, and 6,284,125, which are hereby incorporated by reference in their entirety.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for determining an analyte concentration in a physiological sample, the method comprising the steps of:
   (a) introducing the physiological sample into an electrochemical cell comprising:
      (i) first and second electrodes in a spaced apart relationship; and
      (ii) a reagent layer comprising an enzyme and a mediator;
   (b) detecting the presence of sample in said electrochemical cell;
   (c) applying a first electric potential having a first polarity to the electrochemical cell and measuring cell current as a function of time to obtain a first time-current transient immediately after said detecting step;
   (d) applying a second electric potential having a second polarity to the cell, wherein the second polarity is opposite the first polarity, and measuring cell current as a function of time to obtain a second time-current transient; and
   (e) calculating a first current value from the second time-current transient;
   (f) calculating a second current value from the second time-current transient and a third current value from the first time-current transient;
   (g) calculating a ratio which comprises the second current value divided by the third current value; and
   (h) multiplying the first current value less a background value by the ratio to derive analyte concentration wherein steps (c) through (h) occur in less than about 10 seconds from an occurrence of step (b).

2. The method according to claim 1, wherein steps (c) through (h) occur in less than about 6 seconds.

3. The method according to claim 1, wherein the ratio is to a power p.

4. The method according to claim 1, wherein the first current value is proportional to analyte concentration.

5. The method according to claim 1, wherein the first, second, and third current values comprise an integral of cell current as a function of time.

6. The method according to claim 1, wherein the first, second, and third current values comprise a summation of cell current.

7. The method according to claim 1, wherein the analyte comprises glucose.

8. The method according to claim 1, wherein the physiological sample is a material selected from the group consisting of whole blood, plasma, serum, interstitial fluid, and urine.

9. The method according to claim 1, wherein the second electric potential is applied immediately following the application of the first electric potential.

10. The method according to claim 1, wherein the electrochemical cell has a volume which is less than about 1 microliter.

11. The method according to claim 1, wherein the enzyme is a material chosen from the group consisting of glucose oxidase, glucose dehydrogenase based on a methoxatin co-factor, and glucose dehydrogenase based on a nicotinamide adenine dinucleotide co-factor.

12. The method according to claim 1, wherein the mediator is a material chosen from the group consisting of ferricyanide, ferrocene, ferrocene derivatives, osmium bipyridyl complexes, and quinine derivatives.

13. The method according to claim 1, wherein the first electric potential is applied for a duration time ranging from about 1 second to about 5 seconds.

14. The method according to claim 1, wherein the second electric potential is applied for a duration time ranging from about 1 second to about 5 seconds.

15. The method according to claim 1, wherein the wherein the second and third current values are calculated at different time intervals.

16. The method according to claim 1, wherein the analyte concentration is calculated based upon an equation $[C]=(I_2/I_3)^p * ((a*I_1)-Z)$ where $[C]$ is analyte concentration, $I_1$ is the first current value, $I_2$ is the second current value, $I_3$ is the third current value, and $Z$, $p$ and $a$ are calibration factors.

17. The method according to claim 16, further comprising the step of empirically determining p and a.

18. The method according to claim 16, wherein p is in the range of about 0.2 and 4 and a is equal to about one.

19. The method according to claim 18, wherein p is equal to about one and a is equal to about one.

20. The method according to claim 1, wherein the first electrode and the second electrode comprise a conductive material chosen from the group consisting of gold, palladium, platinum, silver, iridium, doped tin oxide, and carbon.

21. The method according to claim 20, wherein the first electrode is palladium and the second electrode is gold.

22. The method according to claim 20, wherein the conductive material is sputtered onto an insulating sheet.

23. The method according to claim 20, wherein the conductive material is screen-printed onto an insulating sheet.

24. The method according to claim 1, wherein the reagent layer is disposed on the first electrode.

25. The method according to claim 24, wherein the first polarity is negative with respect to the second electrode and the second polarity is positive with respect to the second electrode.

26. The method according to claim 24, wherein the first electric potential ranges from about 0.0 to −0.6 V with respect to the second electrode and the second electric potential ranges from about 0.0 to 0.6 V with respect to the second electrode.

27. A method for determining an analyte concentration in a physiological sample, the method comprising:
   (a) introducing the physiological sample into an electrochemical cell comprising:
      (i) first and second electrodes in a spaced apart relationship; and (ii) a reagent layer comprising an enzyme and a mediator;
(b) detecting the presence of sample in said electrochemical cell;
(c) applying a first electric potential having a first polarity to the cell and measuring cell current as a function of time to obtain a first time-current transient immediately after said detecting step;
(d) applying a second electric potential having a second polarity to the cell, wherein the second polarity is opposite the first polarity, and measuring cell current as a function of time to obtain a second time-current transient; and
(e) calculating a first integrative current value from the first time-current transient and a second integrative current value from the second time-current transient;
(f) calculating a ratio which comprises the second value divided by the first current value;
(g) calculating a correction factor that comprises the ratio;
(h) calculating an initial concentration value from the first and/or second time-current transients; and
(i) multiplying the initial concentration value less a background value by the correction factor to derive the analyte concentration wherein steps (c) through (i) occur in less than about 10 seconds from an occurrence of step (b).

28. The method according to claim 27, wherein the first and second integrative current values comprise an integral of cell current as a function of time.

29. The method according to claim 27, wherein the first and second integrative current values comprise a summation of cell current as a function of time.

30. The method according to claim 27, wherein the analyte is glucose.

31. The method according to claim 27, wherein the physiological sample is a material selected from the group consisting of whole blood, plasma, serum, interstitial fluid, and urine.

32. A method for determining an analyte concentration in a physiological sample, the method comprising:
(a) introducing the physiological sample into an electrochemical cell comprising:
(i) first and second electrodes in a spaced apart relationship; and
(ii) a reagent layer comprising an enzyme and a mediator;
(b) detecting the presence of sample in said electrochemical cell;
(c) applying a first electric potential having a first polarity to the electrochemical cell and measuring cell charge as a function of time to obtain a first time-charge transient immediately after said introducing step;
(d) applying a second electric potential having a second polarity to the cell, wherein the second polarity is opposite the first polarity, and measuring cell charge as a function of time to obtain a second time-charge transient;
(e) calculating a first charge value from the second time-charge transient;
(f) calculating a second charge value from the second time-charge transient and a third charge value from the first time-charge transient;
(g) calculating a ratio based on the second charge value and the third charge value; and
(h) multiplying the first charge value less a background value by the ratio to derive analyte concentration wherein steps (c) through (h) occur in less than about 10 seconds from an occurrence of step (b).

* * * * *